US007650021B2

(12) United States Patent
Braess

(10) Patent No.: US 7,650,021 B2
(45) Date of Patent: Jan. 19, 2010

(54) DEVICE AND METHOD FOR DETERMINING THE CONCENTRATION OF A TRACER IN BLOOD

(75) Inventor: Henning Braess, Lutherville (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 254 days.

(21) Appl. No.: 10/578,447

(22) PCT Filed: Nov. 4, 2004

(86) PCT No.: PCT/IB2004/052299

§ 371 (c)(1),
(2), (4) Date: May 8, 2006

(87) PCT Pub. No.: WO2005/044311

PCT Pub. Date: May 19, 2005

(65) Prior Publication Data

US 2007/0135710 A1 Jun. 14, 2007

(30) Foreign Application Priority Data

Nov. 11, 2003 (EP) .................................. 03104145

(51) Int. Cl.
*G06K 9/00* (2006.01)
*G01T 1/163* (2006.01)
(52) U.S. Cl. ...................... 382/128; 382/130; 382/131; 250/363.05; 250/367; 250/370.09; 600/427
(58) Field of Classification Search ............. 514/12–14; 600/431; 250/363.03, 263.04, 370.09, 367; 382/128, 131, 130
See application file for complete search history.

(56) References Cited

U.S. PATENT DOCUMENTS 5,019,323 A * 5/1991 Lambrecht et al. .......... 376/201
5,608,221 A * 3/1997 Bertelsen et al. ....... 250/363.03

(Continued)

FOREIGN PATENT DOCUMENTS

FR 2 717 909 A1 9/1995

(Continued)

OTHER PUBLICATIONS

Time-of-Flight Positron Emission Tomography: Status Relative to Conventional PET, teaching editorial, vol. 24, No. 1, 2002.*

(Continued)

*Primary Examiner*—Wesley Tucker
*Assistant Examiner*—Nancy Bitar

(57) ABSTRACT

With the aid of an X-ray CT (5, 6), the spatial position (r) of a body cavity that is filled with blood is determined, which for example can be a part of the aorta or of the left ventricle of the heart of a patient (1). Subsequently, a TOF-PET unit that includes two detector elements (3a, 3b) is positioned to place a predefined volume element (2) in the blood filled body cavity. From pairs of annihilation quanta received from the volume element (2) a concentration of the tracer in this volume element (2) and thus in the blood is determined. This concentration can for example be used within the framework of pharmaco-kinetic examinations which are carried out on the patient (1) with the aid of a three-dimensional PET unit (4).

10 Claims, 1 Drawing Sheet

U.S. PATENT DOCUMENTS

| | | | |
|---|---|---|---|
| 6,294,788 B1 * | 9/2001 | Cooke et al. | 250/363.03 |
| 6,327,546 B1 * | 12/2001 | Petrillo et al. | 702/89 |
| 6,346,706 B1 * | 2/2002 | Rogers et al. | 250/363.04 |
| 6,528,793 B1 * | 3/2003 | Chen et al. | 250/363.03 |
| 6,631,284 B2 * | 10/2003 | Nutt et al. | 600/427 |
| 7,057,178 B1 * | 6/2006 | Manjeshwar et al. | 250/363.04 |
| 7,127,095 B2 * | 10/2006 | El Fakhri et al. | 382/128 |
| 7,129,496 B2 * | 10/2006 | Stearns et al. | 250/363.03 |
| 7,132,664 B1 * | 11/2006 | Crosetto | 250/367 |
| 7,173,247 B2 * | 2/2007 | Shah | 250/363.03 |
| 7,180,074 B1 * | 2/2007 | Crosetto | 250/370.09 |
| 7,227,149 B2 * | 6/2007 | Stearns et al. | 250/363.03 |
| 7,265,352 B2 * | 9/2007 | Muehllehner et al. | 250/363.02 |
| 7,381,958 B2 * | 6/2008 | Karp et al. | 250/363.03 |
| 7,381,959 B2 * | 6/2008 | Manjeshwar et al. | 250/363.03 |
| 7,412,280 B2 * | 8/2008 | Hertel et al. | 600/427 |
| 7,518,114 B2 * | 4/2009 | Ganin et al. | 250/363.03 |
| 2004/0195512 A1 * | 10/2004 | Crosetto | 250/363.04 |
| 2005/0257748 A1 * | 11/2005 | Kriesel et al. | 119/51.02 |
| 2007/0040122 A1 * | 2/2007 | Manjeshwar et al. | 250/363.03 |
| 2007/0106154 A1 * | 5/2007 | Conti | 600/436 |
| 2007/0270693 A1 * | 11/2007 | Fiedler et al. | 600/436 |

FOREIGN PATENT DOCUMENTS

FR 2717909 * 9/1995

OTHER PUBLICATIONS

Time of flight in PET revised, IEEE 2003.*

Multifunctional magnetic resonance imaging, of cerebrovascular disease J.van der Grond,W.P.T.M. Mali, 1997.*

Effects of Scintillation Light Collection for Annihilation Quantaon the Time Resolution of a Time-of-Flight Detector, IEEE 1990.*

X-Ray Computed Tomography Methods for In Vivo Evaluation of Local Drug Release Systems, IEEE 2002.*

Positron Emission Tomography With the Use of Time-of-Flight Information ,Chin-Tu Chen et al. Department of Radiology, The University of Chicago Chicago, Illinois 60637, IEEE 1990.*

The imaging science of positron emission tomography Terry Jones, 1996.*

Beckmann, N., et al.; From Anatomy to the Target: Contributions of Magnetic Resonance Imaging to Preclinical Pharmaceutical Research; 2001; The Anatomical Record (New Anat.); vol. 165; pp. 85-100.

Moses, W. W., et al.; Time of Flight in PET Revisited; 2003; IEEE Trans. on Nuclear Science; 50(5)1325-1330.

Paans, A.M.J., et al.; Positron Emission Tomography in Drug Development and Drug Evaluation; 2000; Current Pharmaceutical Design; vol. 6; pp. 1583-1591.

Salem, K. A., et al.; X-Ray Computed Tomography Methods for In Vivo Evaluation of Local Drug Release Systems; 2002; IEEE Trans. on Medical Imaging; 21(10)1310-1316.

Trichard, C., et al.; Binding of Antipsychotic Drugs to Cortical 5-HT2A Receptors: A PET Study of Chlorpromazine, and Amisulpride in Schizophrenic Patients; 1998; American Journal of Psychiatry; 155(4)505-508.

* cited by examiner

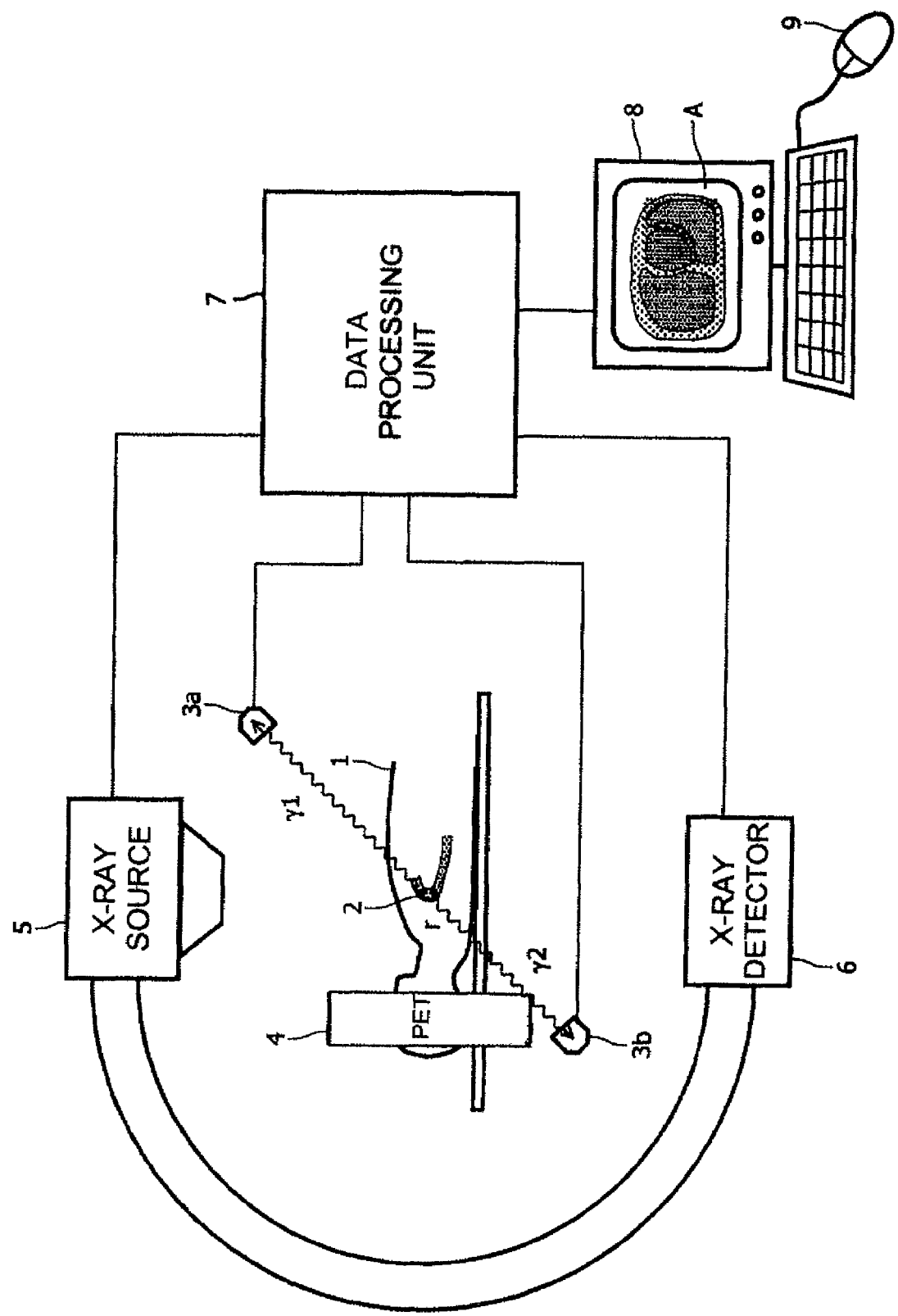

DEVICE AND METHOD FOR DETERMINING THE CONCENTRATION OF A TRACER IN BLOOD

This application relates to device and a method for the in vivo determination of the concentration of a PET tracer in blood.

In the case of Positron Emission Tomography (PET), the distribution of a radionuclide in the body of a patient is determined in that the annihilation quanta produced after the release of positrons are demonstrated. PET measurements are increasingly also used for pharmaco-kinetic modeling, in order to research the mode of the action of drugs. In such examinations, a particular body region is depicted by a PET detector, continuously and in a time-resolved manner, in order to observe dynamically the distribution of a PET tracer (that is, a radioactive marker substance or $\beta^+$ emitter that is appropriate for PET examinations). To evaluate the measurements, it is often necessary to know the concentration of the tracer in the (arterial) blood at all times. This is typically established in an invasive manner, i.e. by taking blood samples.

Against this background, it is an object to provide a means for determining the concentration of a PET tracer in the blood that is simple, less stressful for the patient, and at the same time precise.

One aspect resides in a device which serves for the in vivo determination of the concentration of a PET tracer in the blood of a (human or animal) subject. To this end, it includes the following components:

An image-producing device which permits the locally resolved depiction of a body region. By "locally resolved depiction" we mean a depiction in which at any time of the depiction, the co-ordinates of the corresponding spatial point in the illustrated body region are known or can be determined via known geometrical relations. This condition is fulfilled for example by sectional illustrations produced with a computer tomography device, or by three-dimensional reconstructions of a body volume A TOF-PET unit for recording the concentration of the tracer in a predetermined volume element. According to the definition, the TOF-PET unit (TOF=Time Of Flight) can determine the times of flight or the difference between the times of flight of two gamma quanta from an annihilation process so precisely that on the basis of this information, the point of origin of the quanta can be localized on the line of their flight path. The volume element, which can be observed separately with the TOF-PET unit, preferably has a size of approximately 0.2 to 20 cm$^3$, with a size of approximately 0.5 cm$^3$ to 5 cm$^3$ being particularly preferable.

A data processing unit which is coupled to the image-producing device and the TOF-PET unit. The data processing unit is furthermore set up to set the TOF-PET unit in such a way that the volume element that is recorded with this lies in a body volume filled with blood, wherein the spatial position of this body volume filled with blood is determined with the aid of the image-producing device.

With the device described above, it is possible to measure the concentration of a PET tracer in the blood of a patient continuously and in a non-invasive manner. For this, with the image-producing device, the spatial position of a body volume filled with blood, which can for example be the aorta or the left ventricle of the heart, is determined. With the aid of this information it is then possible to place the volume element observed by the TOF-PET unit directly into the body volume filled with blood, so that the TOF-PET unit exclusively receives signals from the blood. The data of the TOF-PET unit therefore represent the concentration of the tracer in the blood which is sought. An advantage of the device is that no invasive procedure is necessary, which means a corresponding simplification of the examination procedure and less stress on the patient. Furthermore, it is possible specifically to determine the concentration of the tracer in the blood from a particular body region, for example in the arterial blood of the left ventricle of the heart. In the case of blood sampling, on the other hand, as a rule only the concentration of the tracer in the periphery of the blood circulation is accessible. A further advantage results from the use of a TOF-PET unit, in which by setting a time-of-flight window, the position of an examined volume element can be displaced relatively easily along a line through the body of a patient. This enables simple, possibly also dynamic or subsequent fixing of the volume element under examination.

The TOF-PET unit can in principle be formed by a TOF-PET detector which is capable of depicting larger regions such as for example body sections or three-dimensional volumes. However, such a complete detector is not necessary for the desired investigative purpose, and as a rule it is even disadvantageous, for reasons of the space required and the control required. The TOF-PET unit therefore preferably comprises two detector elements, lying opposite one another, for gamma quanta, including the corresponding evaluation electronics unit, which enables the detection of the times of flight of two gamma quanta from an annihilation process. With a TOF-PET unit of this type, it is possible to observe only a narrow (as a rule, pipe-shaped) volume that extends along a line. However, this is adequate for the observation of a volume element filled with blood that lies on the line. Due to the limitation to just two detector elements, such a TOF-PET unit can be produced relatively cheaply and additionally accommodated in an examination laboratory without problems, and in fact for example even in close proximity to an X-ray machine. In particular it is possible in design terms to connect the TOF-PET unit in a fixed manner to a (mobile) X-ray unit, so that there is a known relation between the illustration geometry of the X-ray device and the line of observation of the TOF-PET unit.

The effective area of the detector elements of a TOF-PET unit of the type described above is preferably in each case approximately 10 mm$^2$ to approximately 400 mm$^2$, with approximately 30 mm$^2$ to approximately 100 mm$^2$ being particularly preferred. By "effective area" here we mean the area, standing perpendicular to the connection line of the two detector elements, of the sensitive volume of the detector elements.

The image-producing device can be for example an MRI device and/or an X-ray projection device, in particular an X-ray computer tomography device. Such devices can provide illustrations of body regions with a high level of location resolution, and are already present in many examination laboratories.

According to a further development, the device as described includes a PET device for (preferably three-dimensional) recording of the distribution of the PET tracer in a body region. This body region is typically a different one from that in which the measurement with the TOF-PET unit takes place. For example, through the additional PET device, a three-dimensional depiction of the head of a patient can take place, in order to observe pharmaco-kinetic processes in the brain. The data obtained here can then be combined with the dynamically determined concentration of the PET tracer in the blood.

The data processing unit can optionally be set up to segment a body volume that is filled with blood in one or more illustrations produced by the image-producing device. In this case, the spatial position of this body volume can be automatically determined and the TOF-PET unit can be automatically oriented to this.

According to a further embodiment of the equipment, it includes a display device for depicting illustrations that have been produced with the image-producing device, as well as input means for interactive selection of a body volume in these illustrations. In this case for example, on an illustration produced with the image-producing device, a doctor can specify interactively the body volume filled with blood, whereupon the data processing device determines the spatial position of this body volume and aligns the TOF-PET unit to this.

As has already been mentioned, the body volume filled with blood that is observed by TOF-PET unit can in particular be the aorta or the left ventricle of the heart, so that the concentration of the tracer in the arterial blood can be observed in a targeted manner.

The invention furthermore relates to a method for the in vivo determination of the concentration of a PET tracer in the blood, which comprises the following steps:

production of at least one locally resolved illustration of a body region;

determination of the spatial position of a body volume filled with blood on the basis of the illustration produced;

recording of annihilation quanta coming out of the body volume, taking account of their times of flight.

The method thus contains, in a general form, the steps that can be carried out with equipment of the type explained above. With regard to the details, advantages and further features of the method, we refer to the description given above.

In particular, the method can be further developed such that a dynamic, preferably three-dimensional PET recording of a further body region takes place, and that the data obtained here are combined with the established concentration of the PET tracer in the blood. In this way it is possible to carry out for example pharmaco-kinetic examinations of processes in the brain, which on account of the blood-brain barrier are of great importance, or in other body regions.

The invention may take form in various components and arrangements of components, and in various steps and arrangements of steps. The drawings are only for purposes of illustrating the preferred embodiments and are not to be construed as limiting the invention.

The single FIGURE shows schematically the components of one embodiment of a device for determining the concentration of a tracer in the blood of a patient.

In the case of the example shown, the equipment comprises an X-ray/computer tomography unit, indicated schematically, with an X-ray source 5 and an X-ray detector 6, which are fastened to a C-arm and which can be pivoted with this around a patient 1. The X-ray device is connected to a data processing unit 7 for control and image evaluation. From the projection photos produced in the case of a sweep of the X-ray device, the data processing unit 7 can, in a familiar manner, produce a three-dimensional sectional image A through the body of the patient 1. This sectional image A can for example be represented on a monitor 8 that is connected to the data processing unit 7.

With the aid of input means such as for example a mouse 9 or a keyboard, a doctor can select a body volume filled with blood on such a sectional illustration A. This can be for example the aorta or the left ventricle of the heart, which are respectively filled with arterial blood. Alternatively, the data processing unit 7 can also be set up to segment automatically body volumes filled with blood in the illustrations A, with the aid of appropriate algorithms of image processing.

From the area that has been automatically or interactively set on the illustration A, the data processing unit 7 can then determine the actual spatial position r of a corresponding volume element 2, which is filled with blood, in the body of the patient 1.

The device furthermore comprises a TOF-PET unit, with the detector elements 3a and 3b that form it being shown only schematically in the FIGURE. These detector elements 3a, 3b lie opposite one another on different sides of the body of the patient 1, and can respectively demonstrate gamma quanta that hit them. The structure of such detector elements, which can for example include scintillation crystals of $BaF_2$ and photomultipliers, is known and therefore need not be described in any further detail here.

The detector elements 3a, 3b include in each case an evaluation electronics unit for the pre-processing of the measured signals, and are connected to the data processing unit 7. Through corresponding specification of filter parameters, it can be achieved that from the relatively numerous events demonstrated by the detector elements 3a, 3b, those ones are selected that are attributable to two gamma quanta $\gamma_1$, $\gamma_2$ of an annihilation process. Such quantum pairs arise when due to the radioactive decay of a tracer injected into the blood of the patient 1, a positron is released and [is] annihilated with an electron. The energy of the gamma quanta $\gamma_1$, $\gamma_2$ that arise here is about the same size and its direction of flight is approximately diametrically opposed. Thus if at the two detector elements 3a, 3b, gamma quanta of the appropriate energy are demonstrated at around the same time, it is assumed that these originate from an annihilation process. The point of origin of these gamma quanta $\gamma_1$, $\gamma_2$ must lie on the connection line of the demonstration points in the detector elements 3a, 3b, the so-called "reaction line".

Since, according to the conditions, this must be a TOF-PET unit, the detector elements 3a, 3b have a very high time resolution. This allows differences in time of flight between the gamma quanta $\gamma_1$, $\gamma_2$ of an annihilation pair to be measured, from which then a more precise conclusion can be drawn as to the location of the origin of these gamma quanta on the reaction line. The volume element observed by the TOF-PET unit can therefore be positioned anywhere along the reaction line, by specifying a window for the time of flight differences. For example, the observed volume element in the case of a time-of-flight difference of around zero lies precisely in the middle between the two detector elements 3a, 3b. In particular, the volume element 2 observed by the TOF-PET unit can be placed at the location r that is determined with the CT 5, 6, as described above, so that it lies entirely within a body volume filled with blood. This ensures that the TOF-PET unit measures the concentration of the tracer in the blood precisely.

The position r of the volume element 2 observed with the TOF-PET unit can optionally be checked and adjusted from time to time through photos with the CT 5, 6. It is furthermore conceivable to record the cardiac activity continuously through an electrocardiogram, and to use the measured values of the TOF-PET unit only from certain heartbeat phases, in order to ensure that the heart was in a particular position in which the observed volume element is completely filled with blood.

Also indicated schematically in the FIGURE is a PET detector 4, with which three-dimensional PET images of the brain of the patient 1 can be made. On these images, it is possible to follow dynamically the distribution of the tracer. In order to be able to derive meaningful pharmaco-kinetic models from such observations, it is frequently necessary at the same time to know the concentration of the tracer in the arterial blood (so-called "arterial input function"). This information can advantageously be determined in the case of the equipment presented here, by the TOF-PET unit, as explained above.

The invention has been described with reference to the preferred embodiments. Modifications and alterations may occur to others upon reading and understanding the preceding detailed description. It is intended that the invention be construed as including all such modifications and alterations insofar as they come within the scope of the appended claims or the equivalents thereof.

I claim:

1. A device for in vivo determination of a concentration of a PET tracer in blood, including:
   an image-producing device which generates a locally resolved depiction of a region of the body including a body volume that is filled with blood;
   a TOF-PET unit for recording the concentration of the PET tracer in a predetermined volume element;
   a data processing unit which is coupled to the image-producing device and the TOF-PET unit, the data processing unit in conjunction with the image-producing device determines a spatial position of the body volume that is filled with blood and determines detector element positions of the TOF-PET unit such that the volume element of the TOF-PET unit lies in the body volume that is filled with blood.

2. The device as claimed in claim 1, wherein the TOF-PET unit comprises:
   two γ detector elements that detect pairs of annihilation quanta, the two γ detector elements lie opposite one another and define the predetermined volume element on a line therebetween, and
   corresponding evaluation electronics unit for recording times of flight of the pairs of detected annihilation quanta.

3. The device as claimed in claim 2, wherein the effective area of each detector element is between 10 mm$^2$ and 400 mm$^2$.

4. The device as claimed in claim 1, wherein the image-producing device includes one of an MRI device and an X-ray projection device.

5. The device as claimed in claim 1, further including a 3D PET device which records a three-dimensional distribution of the PET tracer in a body region.

6. The device as claimed in claim 1, wherein the data processing unit segments images produced by the image-producing device to identify the body volume that is filled with blood.

7. The device as claimed in claim 1, further including a display device for displaying images that have been produced with the image-producing device and an input means for interactive selection of a body volume in the displayed images.

8. The device as claimed in claim 1, wherein the body volume filled with blood lies in an aorta or in a left ventricle of a heart.

9. The device as claimed in claim 2, wherein the TOF-PET unit includes only two detector elements to detect annihilation quanta pairs travelling along the line therebetween.

10. The device as claimed in claim 2, wherein the data processing unit further controls positioning the two γ detector elements such that the volume element on the line therebetween lies in the body volume.

* * * * *